United States Patent [19]
Matschke

[11] Patent Number: 5,612,001
[45] Date of Patent: Mar. 18, 1997

[54] APPARATUS AND METHOD FOR GERMICIDAL CLEANSING OF AIR

[76] Inventor: Arthur L. Matschke, P.O. Box 266, Centerbrook, Conn. 06409

[21] Appl. No.: 538,447

[22] Filed: Oct. 3, 1995

Related U.S. Application Data

[63] Continuation-in-part of Ser. No. 211,796, Jun. 15, 1994, Pat. No. 5,498,394, which is a continuation of Ser. No. 778,737, Oct. 18, 1991, Pat. No. 5,216,251.

[51] Int. Cl.[6] .................................................. A61L 9/20
[52] U.S. Cl. ........................... 422/121; 422/111; 422/24; 55/279; 250/455.11
[58] Field of Search .............................. 422/24, 108, 110, 422/111, 121; 55/279; 250/455.11

[56] References Cited

U.S. PATENT DOCUMENTS

| | | | |
|---|---|---|---|
| 2,814,081 | 11/1957 | Stevenson | 21/91 |
| 3,117,832 | 1/1964 | Thomas | 21/58 |
| 3,674,421 | 7/1972 | Decupper | 422/121 |
| 3,683,638 | 8/1972 | Devon | 62/264 |
| 3,744,216 | 7/1973 | Halloran | 422/121 X |
| 3,827,862 | 8/1974 | Berplant | 422/121 |
| 3,877,437 | 4/1975 | Maitan et al. | 128/373 |
| 4,087,925 | 5/1978 | Bienek | |
| 4,201,916 | 5/1980 | Ellner | 250/372 |
| 4,786,812 | 11/1988 | Humphreys | 250/455 |
| 4,877,964 | 10/1989 | Tanaka et al. | 250/455 |
| 4,882,496 | 11/1989 | Bellotti et al. | 250/455.1 |
| 4,948,980 | 8/1990 | Wedekamp | 422/24 X |
| 5,041,825 | 8/1991 | Hart et al. | 340/825.06 |
| 5,216,251 | 6/1993 | Matschke | 250/455 |
| 5,399,319 | 3/1995 | Schoenberger et al. | 422/121 |

Primary Examiner—Robert J. Warden
Assistant Examiner—E. Leigh Dawson
Attorney, Agent, or Firm—Bazerman & Drangel, P.C.

[57] ABSTRACT

A germicidal air cleansing apparatus having an internal ellipsoid chamber which contains UV lamps along the major axis of the ellipsoid. Each of the ends of the ellipsoid along its major axis has an opening to allow the entry and exit of air from the surrounding environment. The chamber is formed from an ultraviolet reflective material such as spun aluminum to allow uniform dispersion of the ultraviolet radiation throughout the chamber. Air is drawn into the chamber by fans at a speed to assure a high kill rate of microorganisms present in the air.

9 Claims, 7 Drawing Sheets

APPARATUS AND METHOD FOR GERMICIDAL CLEANSING OF AIR

BACKGROUND OF THE INVENTION

This application is a continuation-in-part of previously filed application Ser. No. 08/211,796, filed Jun. 15, 1994, and now U.S. Pat. No. 5,498,394, which in turn is a continuation of Ser. No. 778,737, filed Oct. 18, 1991, now U.S. Pat. No. 5,216,251, issued on Jun. 1, 1993.

Airborne bacteria or other microorganisms permeate the air we breath. In a medical environment, such as in a hospital or an operating room, it is particularly important that such airborne organisms be killed. This is both because such environments have a high degree of pathogens, such as tuberculosis, forming part of the atmosphere and because of the susceptibility of already weakened patients including patients having various forms of immune system impairments.

Much effort has gone into trying to limit or destroy atmospheric pathogens, particularly in hospital environments. It has long been recognized that pathogens can be destroyed in the air if they are irradiated with ultraviolet (UV) light and the wavelength of 253.7 nanometers. In order for the UV light to kill microorganisms, and particularly pathogens, the rays must directly strike them. Because of the absolute necessity for antiseptic surroundings, UV lamps of the required wavelength are often used in operating rooms, wards, and nurseries of hospitals. Such UV lamps are fixed to walls or ceilings.

The exposure to UV light necessary to kill microorganisms (or the "kill" factor) is a product of time and intensity. However, due to the dangers to humans of radiation from wide-spread use of UV lamps, exposure of human beings to UV light has been limited by government regulations and medical practice.

The current exposure limits (ACGIH, NIOSH standard) for 254 m ultraviolet germicidal wavelength ceiling fixtures is 6000 μwatts seconds/cm$^2$ in one eight hour day. Thus the maximum allowed intensity per second is 0.2 μW/cm$^2$. At this intensity, eight hours at the allowed exposure level is required to again 90% kill of *Mycobacterium tuberculosis* (90% kill-value=6200 μwatts/cm$^2$) at head height. For 100% kill using the same standard, the value is 10,000 μwatts/cm$^2$, requiring 13.89 hours of exposure. These long exposure times permit migration of microorganisms out of range of the UV lamp and result in accumulation of microorganisms which survive the UV lamp in the room. Increasing air throughput in the room (i.e., increasing air circulation) does not increase exposure to the UV lamp. It only displaces the microorganisms away from the UV lamp without sufficient exposure. Favorable displacement, e.g., air being constantly brought nearer the UV lamp thereby reducing irradiation times, does not consistently occur.

To overcome these problems, there have been various attempts to circulate air passed UV sources in a chamber which acts to shield the UV radiation from the room's occupants. None of these chambers have, however, been designed to evenly concentrate the radiation from the UV sources in a limited air passage such that high kill rates are obtained throughout the entire air volume being irradiated. They have not used UV reflective surfaces throughout their shielded chamber to so distribute the UV radiation. Equally, these designs have failed to operate a high enough throughput with high kill rates to assure constant and complete treatment of the air in a room, nor have they been able to operate at efficiency rates and noise levels to make them practical in environments such as hospitals, operating rooms or living environments of high risk patients such as AIDS victims.

For example, U.S. Pat. No. 4,786,812 to Humphries, issued Nov. 22, 1988, discloses a light-weight and portable germ killing machine which attempts to deal with the limitations of conventional UV lamps. This machine has a plurality of ultraviolet light bulbs fixed inside of a protective and light-shielded housing and adjacent to a reflective surface with air passages. A fan is located near the reflective surface and draws air from immediately around the housing toward and around the UV bulbs. Filters are located along the sides and underside to block out potentially damaging items. This apparatus is used to draw air and germs up from carpets or other adjacent surfaces as the machine is moved over a surface. The machine may also have an attachment to flush out germs hidden behind objects. It does not provide the necessary levels of throughput, high kill rate and uniform irradiation required for the continuous removal of airborne microorganisms throughout a room.

U.S. Pat. No. 5,216,251, issued on Jun. 1, 1993, by the present inventor, and a grandparent of the present application, is directed to a bio-conditioning, germicidal dryer, which discloses a dryer having two ports which allow the hands to comfortably extend laterally into the chamber in which UV light is irradiated. The chamber in the earlier invention was shaped to uniformly distribute rays of ultraviolet light throughout the working chamber. This device, however, was not designed for the continuous cleansing of air in a room, but rather the germicidal cleansing of hands or other objects placed in the chamber. There is positive pressure in the chamber which does generate a small air flow to the environment. It is, however, not sufficient to cleanse the air in a room.

SUMMARY OF THE INVENTION

It is an object of the present invention to provide an ultraviolet light chamber for processing air in a room which combines both optics and air-flow techniques to kill microorganisms present in the air.

It is a further object of the present invention to do so with no ultraviolet exposure to room occupants.

It is a further object of the present invention to filter the air to minimize airborne particulates, thereby raising the illumination level throughout the serviceable UV lamp life.

It is a further object of the present invention to cause a high percentage of the air in the room to be periodically circulated passed a UV source without subjecting the people in the room to raised UV radiation levels.

It is a further object of the present invention to cause room air to be exposed at a uniform constant rate to high levels of ultraviolet radiation.

It is further an object of the present invention to provide apparatus and method for the germicidal cleansing of air in a hospital room, operating room or in a sensitive environment such as a living environment of a person with an immune deficient system.

In the present invention, the room air is circulated through and the attended airborne bacteria and viruses are drawn into a chamber designed to achieve uniform dispersal of ultraviolet rays throughout. The microorganisms present are exposed to high intensity ultraviolet rays, thousands of times greater than the ultraviolet standard for room occupancy or operating rooms. Filters remove particulates and keep ultraviolet lamps efficient and operating at design specifications throughout the life of the machine.

The chamber is formed from spun aluminum. The chamber cross-section is that of an ellipse, i.e., it is ellipsoid, with the major axis of the ellipse being the direction through which the air is drawn. Such elliptical design causes uniform irradiation as the air passes through the chamber.

The chamber has an opening at each end which has a displaced parabola end caps such that they form an addendum to the original ellipse, both the chamber and the end caps having common foci. Air is allowed to enter and leave through the ends of the chamber while the end caps allow the reflection of the ultraviolet back into the chamber. The design of the chamber assures that ultraviolet energy is uniformly distributed throughout, any isolated point in the chamber having an identical energy level as any other point. The chamber is sized to allow the air flow necessary to circulate all the air in the room through the chamber in a fixed, relatively short time while assuring the desired kill rate.

Since reduced temperatures effect germicidal killing efficiency, the fan speed is automatically lowered to maintain high kill rate as the temperature falls. The fan speed is also automatically adjusted to compensate for increased and decreased occupancy of the room. Filters are used at the beginning of the air flow to remove airborne particulates to thereby prevent contamination of the chamber effecting luminescence and reflectance.

DETAILED DESCRIPTION OF THE PREFERRED EMBODIMENT

The Apparatus

Figure 1:
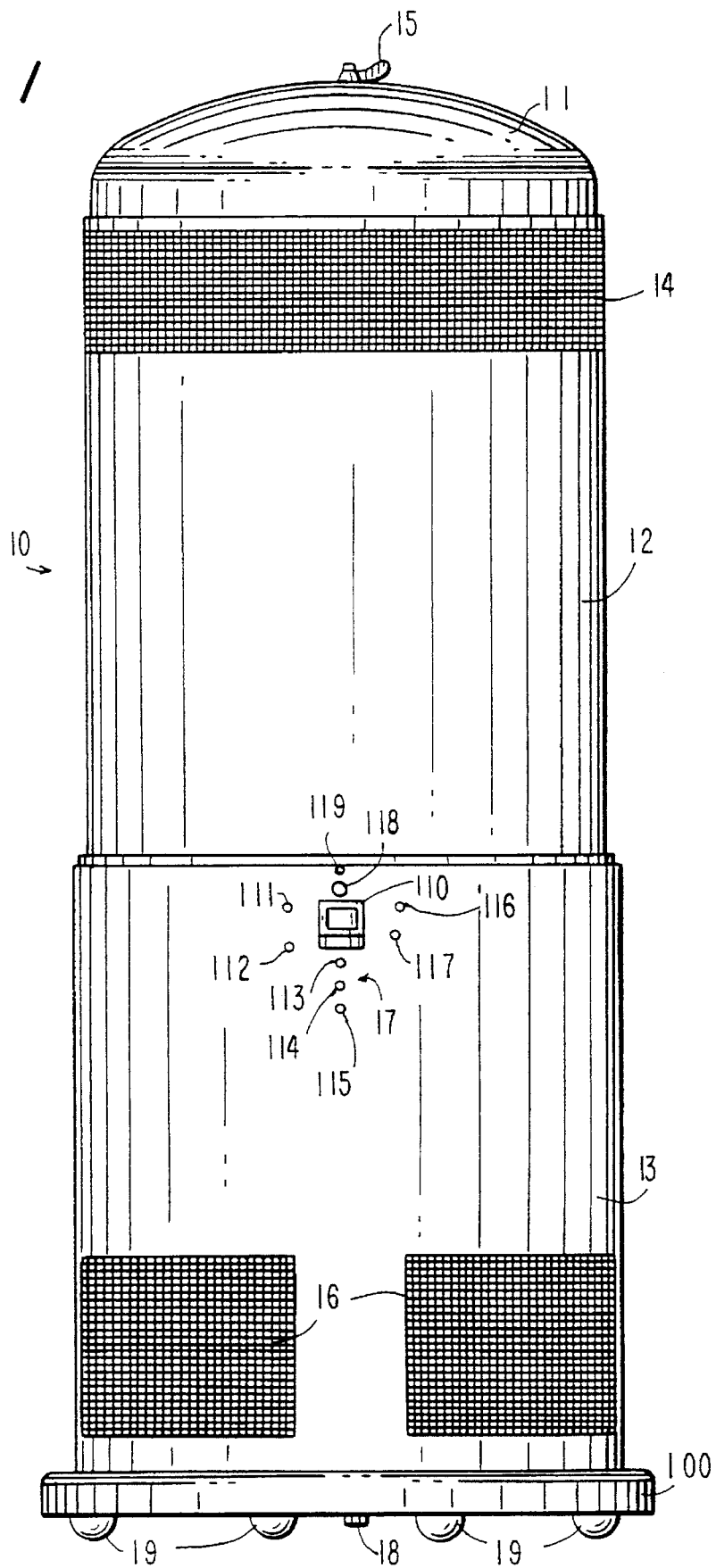
FIG. 1 is a perspective view of the germicidal air cleansing chamber of the present invention.
Figure 8:
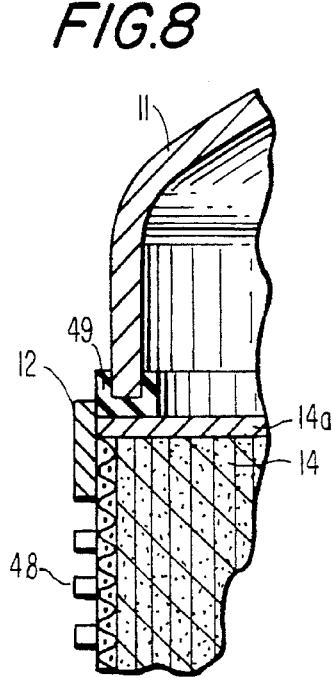
FIG. 8 is an enlarged partial cross-sectional view of the present invention showing the interconnection of the filter with the top of the housing of the present invention.

The housing 10 of the germicidal air cleansing apparatus of the present invention, in general, is formed from a series of concentric cylindrical sub-components. As seen in FIG. 1, the outer housing 10 of the present invention consisting of a housing cap 11, an upper housing 12, and a lower housing 13. A filter 14, to treat incoming air, is positioned behind a grille 48 in the upper housing 12. As seen in FIG. 8, a silicon gasket 49 may be positioned between the housing cap 11 and the top of filter 14. Grilles 16 in lower housing 13 allow the air which has been treated by UV irradiation to be directed back into the room. The controls and indicator lights for the germicidal air cleansing housing 10 are found in the lower housing 13 at 17. The housing 21 may be mounted on rollers 19 attached to platform 100 so that it may be easily moved from room to room as necessary.

As seen more fully in FIGS. 2 and 4–11, central threaded rod 20 forms the backbone on which the germicidal air cleansing chamber 21 of the present invention is built. At its bottom end, central threaded rod 20 has an end nut 18 positioned underneath the bottom platform 100 of the housing 10. A threaded tightening handle 15 is positioned at the other end of the central threaded rod 20 in contact with housing cap 11. The tightening handle 15 can act to tighten or loosen certain of the elements positioned around the central threaded rod 20. The reflective chamber 21 is formed from upper chamber section cap 22, upper chamber section 23, middle chamber section 24, lower chamber section 25 and lower chamber section cap 26. These elements forming chamber section 21 are made from spun aluminum. Due to the inherent characteristics of aluminum and the characteristics resulting from its spinning, such material is particularly suitable to form UV reflective walls.

Figure 3:
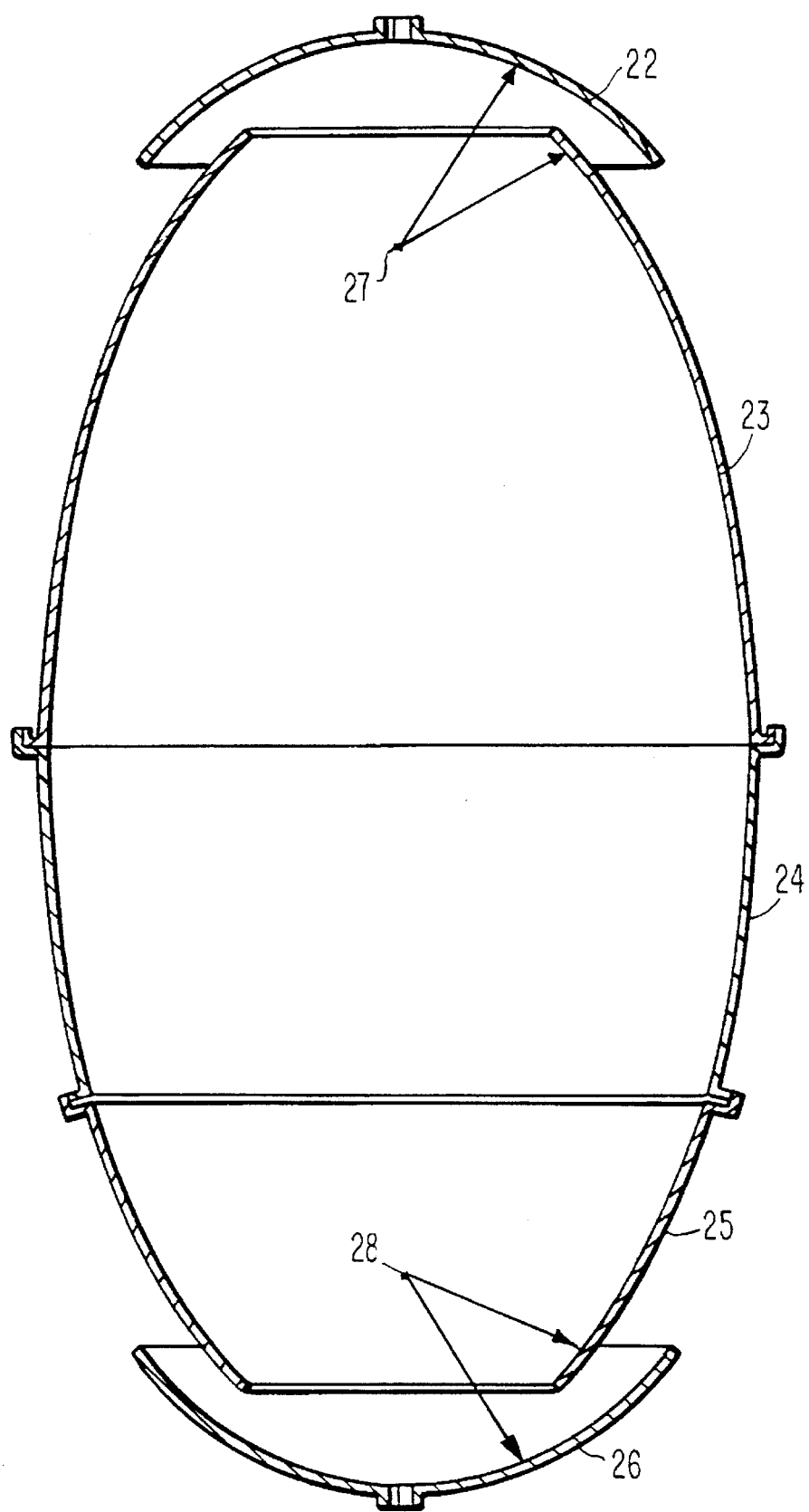
FIG. 3 is a partial front elevational view of the chamber walls showing the common foci between the chamber and the end caps of the chamber.

As seen more clearly in FIG. 3, the chamber 21 is ellipsoid. The upper and lower end caps 22 and 26 are displaced paraboloids which share common loci 27 and 28 with the chamber 21. This assures that any UV light which leaves the chamber 21 is reflected back in the chamber section 21.

A fan bulkhead 33 is positioned around central threaded rod 20 in lower housing 13 immediately above grilles 16. The fan bulkhead 33 is attached to lower housing 13 at its outer edge. There are two fans, 31 and 32, positioned on the fan bulkhead 33. Ballast 130 for UV lamps 60–65 may also be mounted on the fan bulkhead 33. A separate deck assembly 30 above the fan bulkhead 33 holds the electronic circuitry 35 which regulates the operation of the germicidal air cleanser of the present invention. It is supported above fan bulkhead 33 on central threaded rod 20 by support nut 101. The bottom chamber section cap 26 is abutted by nut 34 mounted on central threaded rod 20. The lower chamber section cap 26 supports and is spaced from the lower chamber section 25 by cylindrical spacers 36 and 37. The lower chamber section 25, in turn, supports the middle chamber section 24 and the middle chamber section 24 supports the upper chamber section 23. The upper chamber section cap 22 is supported by cylindrical spacers 38 and 39. Spacers 36, 37, 38 and 39 are of a size and height to provide sufficient space to allow air to pass between their respective chamber section caps 22 and 26 and into the chamber 21.

Figure 9:
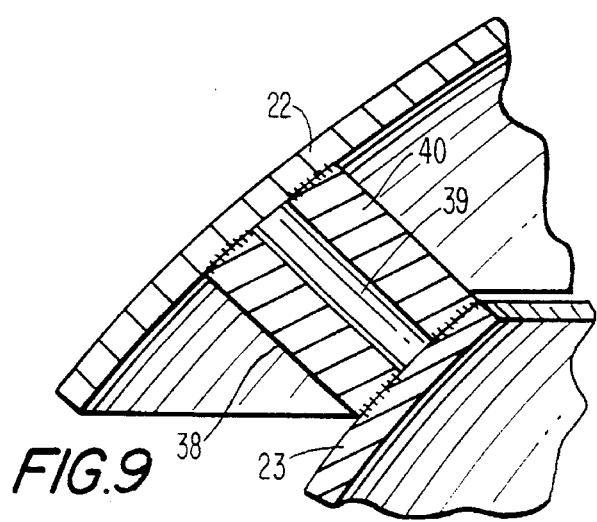
FIG. 9 is an enlarged partial cross-sectional view showing the mating of the chamber and end cap of the chamber of the present invention.
Figure 5:
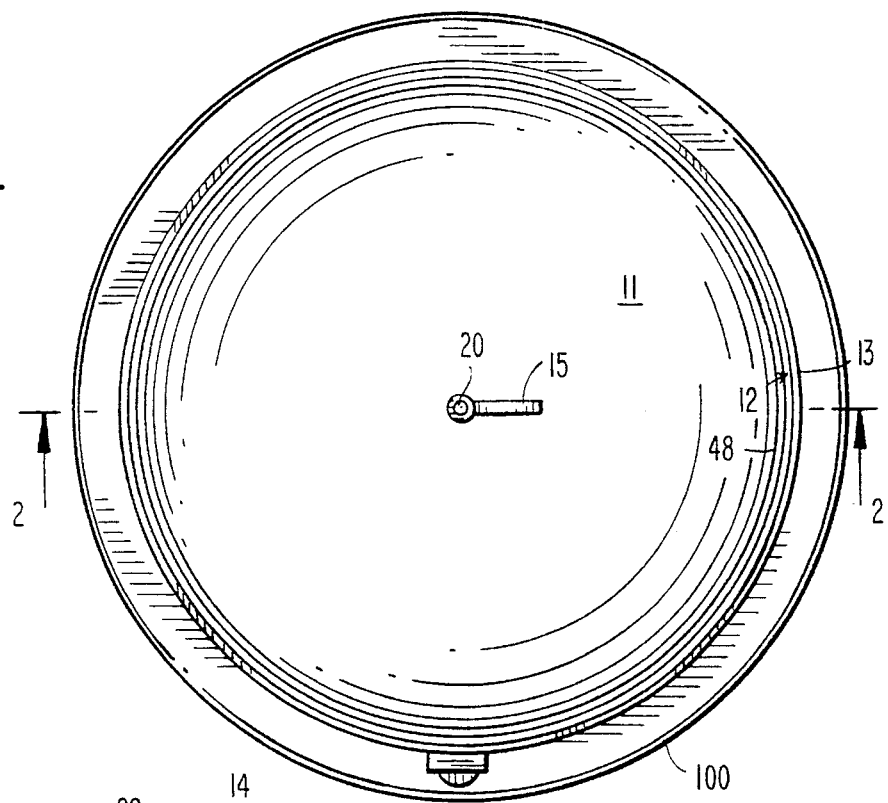
FIG. 5 is a top view of the chamber.
Figure 10:
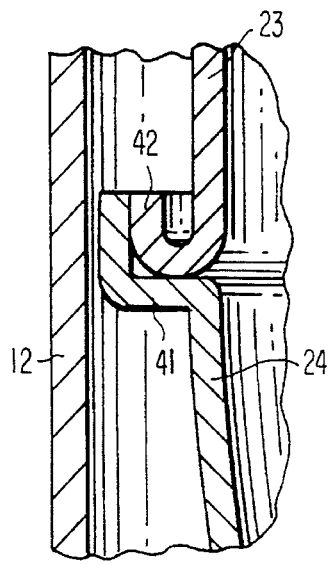
FIG. 10 is an enlarged partial cross-sectional view showing the intersection of the upper half of the chamber with the lower half of the chamber in relation to the outer housing.
Figure 11:
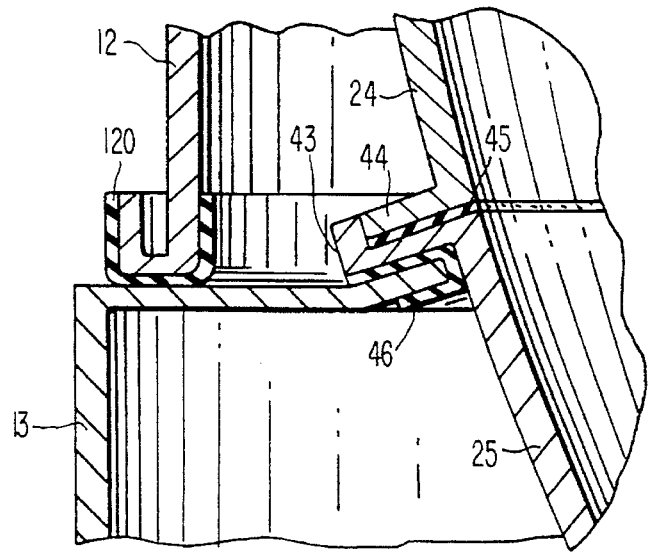
FIG. 11 is an enlarged partial cross-sectional view showing the intersection of the middle portion of the chamber with the lower portion of the chamber and its interaction with the outer housing of the chamber.
Figure 12:
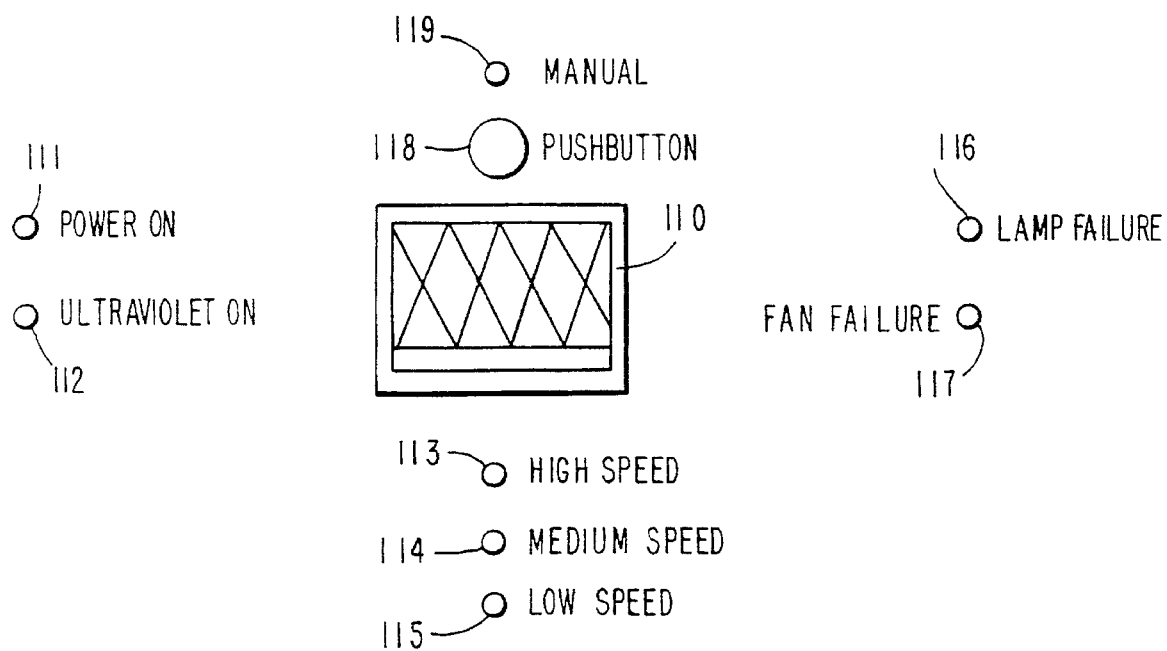
FIG. 12 is a partial view showing the operating buttons and indicators of the present invention.

The details of the construction of the chamber 21 are shown in FIGS. 9, 10 and 11. As seen in FIG. 9, spacer 38 is in the form of a cylindrical wall 40 having a hollow center 39. The spacer 38 is welded in position between upper chamber section cap 22 and the upper chamber section 23. Spacers 36, 37 and 39 are similarly positioned and fixed between respective chamber section cap 26 and chamber 21. As seen in FIG. 10, the upper chamber section 23 is joined to the middle chamber section 24 by an annular shoulder 41 in middle chamber section 24 into which is set a corresponding U-shaped rim 42 of upper chamber section 23. As seen in FIG. 11, the middle chamber section 24 mates with lower chamber section 25 through their respective lips 43 and 44. Lip 43 is held firm against the mating edge of lower housing 13 with nut 34. Silicon gaskets 45, 46 and 120 may be positioned between the various lips to seal the joints between middle chamber section 24 and lower chamber section 25 and between upper housing 12 and lower housing 13 against the passage of air and minimize vibration.

Figure 2:
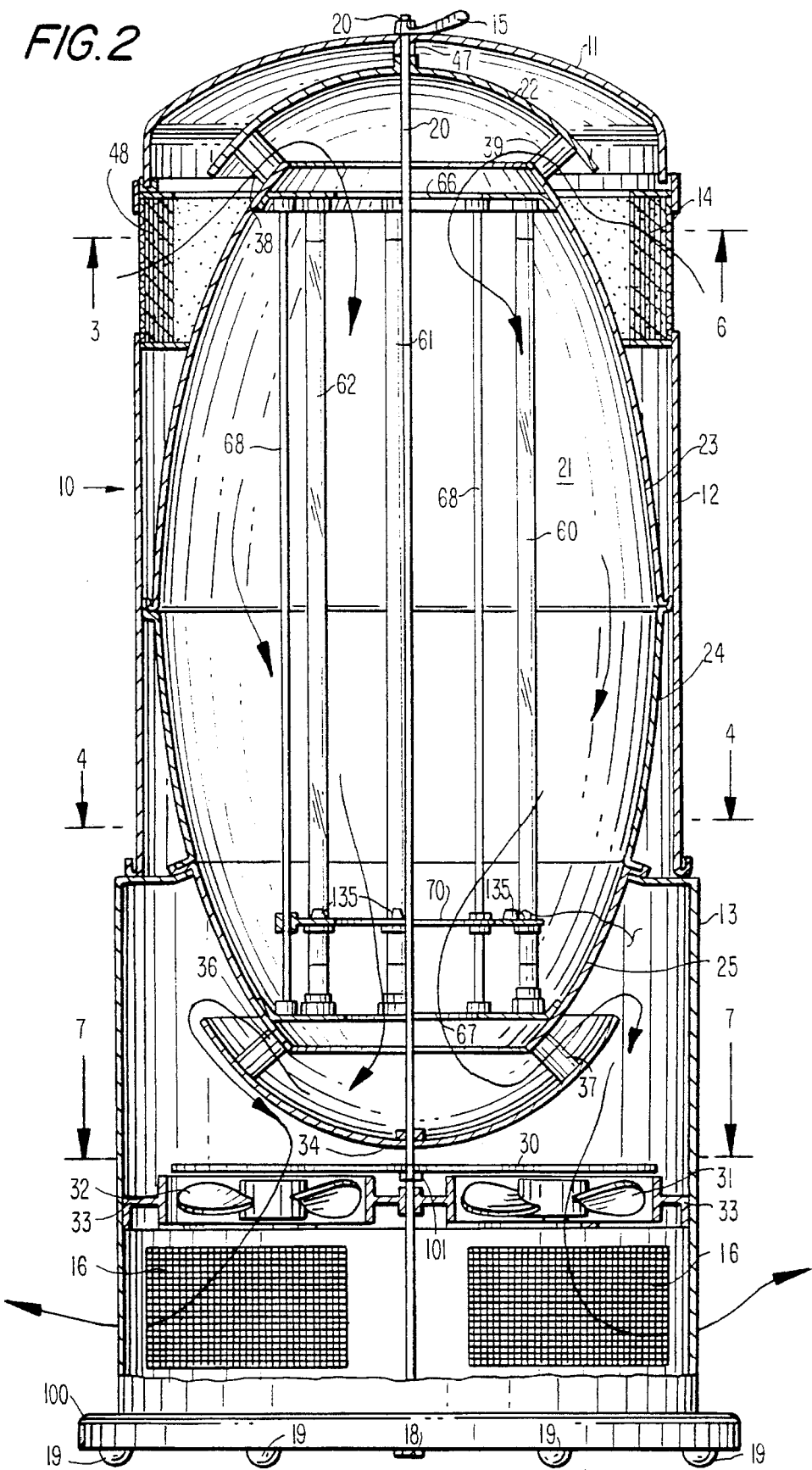
FIG. 2 is a cross-sectional view of the present invention taken at section 2—2 of FIG. 5 with arrows representing the air flow patterns in the apparatus.
Figure 4:
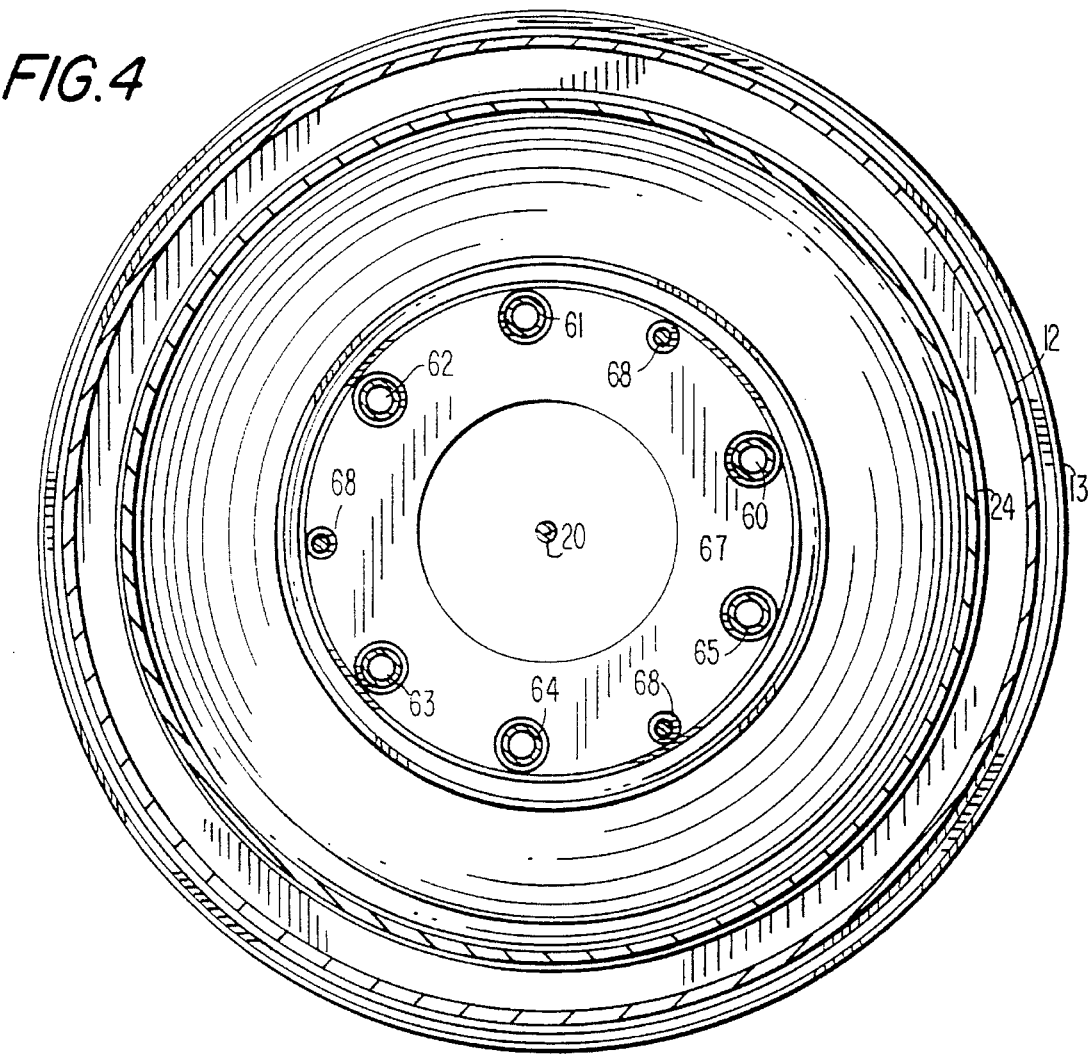
FIG. 4 is a cross-sectional view of the present invention taken at section 4—4 of FIG. 2.
Figure 6:
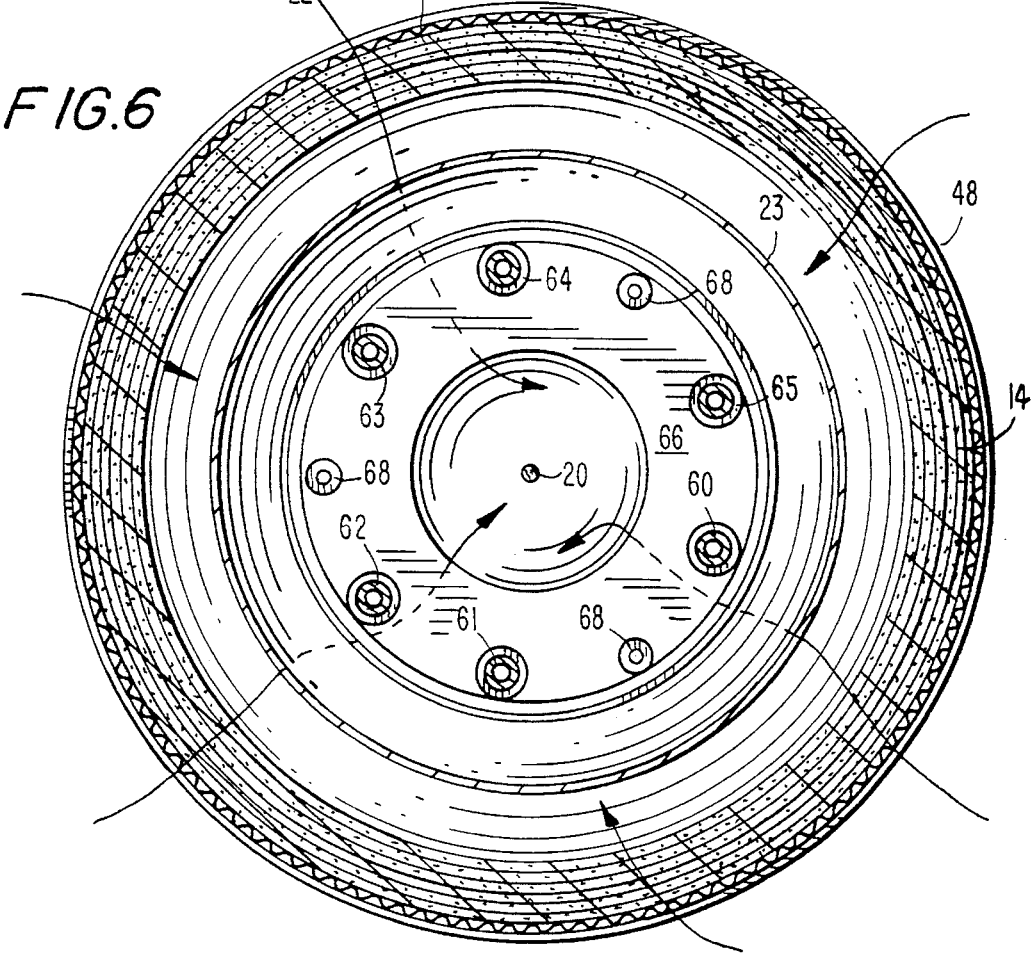
FIG. 6 is a cross-sectional view of the present invention taken at section 6—6 of FIG. 2.
Figure 7:
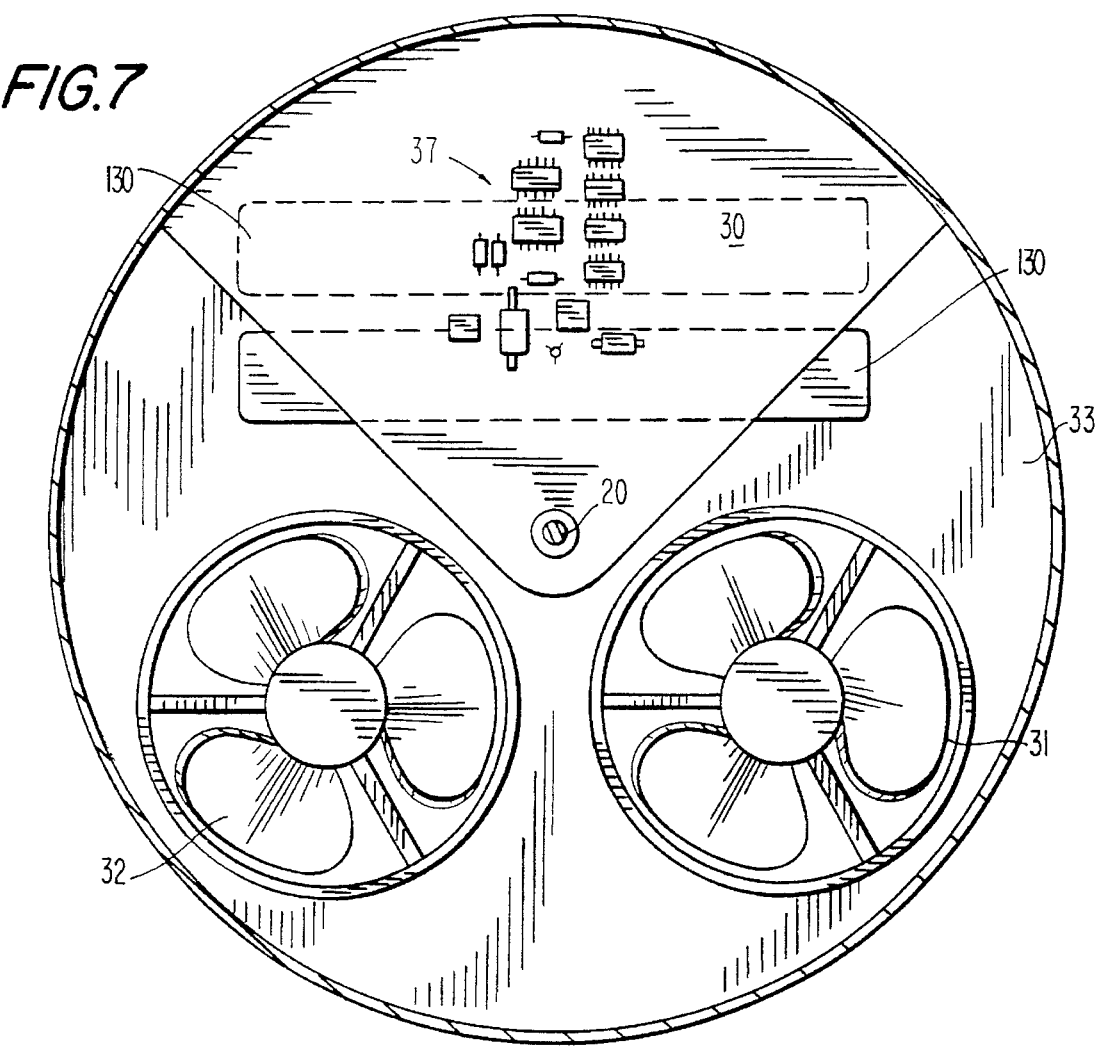
FIG. 7 is a cross-sectional view taken at section 7—7 of FIG. 2.

As seen most clearly in FIGS. 2, 4 and 6 mounted in the chamber are six UV lamps 60–65. The UV lamps 60–65 are mounted between an upper mounting ring 66 and a lower mounting ring 67. Lower mounting ring 67 rests against and is supported by lower chamber section 25. Upper mounting ring 66 and lower mounting ring 67 are positioned around central threaded rod 20. Supports 68 position and hold upper mounting ring 66 in position against the upper chamber section 23. Horizontal support 70 may be added for further stability and is used to mount the lamp performance detectors 135 at each UV lamp 60–65.

As seen in FIG. 1, the controls and indicators 17 are positioned in lower housing 13. The control section has a infrared motion sensor 110 which senses the human traffic flow in the room in which the germicidal air cleanser of the present invention is located. The sensor 110 includes an adjustment (not shown) for range sensitivity for larger or smaller rooms. As will be discussed more fully in the operation section, the sensor 110 will act to control the operation of the fans and, thus, the air flow will be adjusted according to traffic conditions, i.e., when there is no moving traffic in the area, the air flow will operate at the lowest speed sufficient for nighttime air purification under most circumstances, and, as the traffic increases, this speed of operation will, accordingly, increase. A "power on" indicator light 111 is positioned in the panel to signal if power is flowing to the machine. An ultraviolet "on" indicator light 112 is positioned directly below. This light indicates when the ultraviolet lamps are on. Speed indicator lights 113, 114 and 115 are positioned directly below the sensor 110 and indicate whether the fans are running at low, medium or high speed and, thus, whether the throughput of the machine is at low, medium or high levels. A lamp failure indicator light 116 and a fan failure light 117 are located to the right of sensor 110. The lamp failure light 116 will blink on a count to match the lamp number that has failed. Above the sensor 110 is positioned a push button 118 which will place the machine on a manual high speed operation. Directly above the manual high speed push button 118 is an indicator light 119 which indicates manual operation. The on/off button (not shown) is positioned on the opposite side of the lower housing 13.

The Operation

In operation, once turned on, ambient air is drawn by fans 31 and 32 through filter 14 into chamber 21. The air passes through the inlet formed between chamber section cap 22 and upper chamber section 23. Chamber 21 is illuminated with UV light by UV lamps 60–65. As noted previously, chamber 21 is an ellipsoid made of UV radiation reflective walls. The ray path of an ellipse (i.e., the cross-section of an ellipsoid along its major axis) is the "perfect reflector," compensating for reflective angle as a function of distance. Chamber section caps 22 and 26 are displaced paraboloids having the same foci as chamber 21 but having a greater radius. The UV light generated by UV lamps 60–65 is evenly dispersed throughout the extended length of chamber 21. Any point in chamber 21 receives the same quantity of UV light in all directions as any other point within chamber 21. The formation of the walls of chamber 21 by spinning and, the qualities of aluminum from which it is spun, act to insure that the greatest part of the energy generated by UV lamps 60–65 is reflected back into chamber 21 rather than being absorbed by the walls of chamber 21. As an ellipsoid, chamber 21 has a long exposure path for extended UV radiation treatment of the air.

The kill rate is dependent on both the intensity and the length of exposure to the UV radiation. If UV radiation was not evenly dispersed throughout the chamber, the amount of exposure and, thus, the kill rate would vary across chamber 21. Here, due to the design of chamber 21 and the positioning of the light sources longitudinally along chamber 21, parallel to the extended main axis of the ellipses forming the longitudinal cross-section of chamber 21, the kill rate is both high and constant for all air passing through the extended air path through chamber 21.

The total energy in chamber 21 can be calculated based upon UV lamps 60–65 output. For example, commercially available UV lamps specify an output of 13.8 watts (i.e., 13.8 joules/sec.) of ultraviolet energy. After a period of initial use of several hundred hours, there will be an output degradation of 20%. Since the output of the UV lamp is retained within chamber 21, aside from the amount absorbed by the walls of the chamber, calculating the power being delivered to the chamber is relatively simple. If six (6) such lamps are placed within chamber 21, the total power being delivered to chamber 21 would equal approximately 72.8 watts (72.8 joules/sec.) of UV radiation or after degradation, approximately 65 watts or 65 joules/sec. In the spun aluminum chamber 21 of the present invention, approximately 10% of that energy is absorbed by the internal structural components and not the receiving air, leaving an average energy input of 58.5 watts (58.5 joules/sec.) into chamber 21. Due to the energy retaining property of the reflective chamber 21, i.e., its high UV reflective properties, the actual energy in the chamber will accumulate over time and reach a steady state condition at a level above the power level of the UV source.

The other factor in determining kill rate is the length of time the air is exposed inside the chamber 21. As an example, a chamber 21, in accordance with the present invention, could have a volume of 6.453 ft.$^3$ At medium level, the fans 31 and 32 would propel the air through the chamber at approximately 8.333 ft.$^3$/sec. or 500 ft.$^3$/min., approximately equal to the air conditioning industrial standard of approximately 400 ft.$^3$/min. for each ton of air conditioning. Under these conditions, an average 4-bed ward room size of approximately 30'×30' by 11' high would have all of the air in the room exchanged every 20 minutes.

At this rate, any particular molecule of air will be in chamber 21, and exposed to radiation, for approximately 0.77 seconds. In this time, the air is exposed to a minimum of approximately 58.5 joules of UV energy for 0.77 sec., receiving a minimum of approximately 45 joules of UV energy. This amount is constant and the minimum ultraviolet exposure for any air passing through chamber 21. This is extremely high exposure relative to 100% kill rates by ultraviolet (i.e., 10,000 µwatts or 0.01 joules/sec. to kill tubercular bacilli).

When there is a need for increased air flow, such as when there is high traffic in the room in question, the chamber speeds can be set to approximately 700 ft.³/sec. Even at this rate, air is exposed for at least 0.55 sec. and receives approximately a minimum of 32 joules, well above the normal kill rate of 0.01 joules/see. for such microorganisms as tuberculosis bacilli.

In operation, in one embodiment for small room health care use, it is intended that the fans operate at three different speeds. The high speed which will move air through the chamber at 700 ft.³/min., a medium speed which will move air through chamber 21 at 500 ft.³/min. and a low speed of 200 ft.³/min.

The speed will automatically vary under conditions of traffic and temperature to assure an appropriate operating speed depending on conditions of traffic and temperature in the room. The speed of operation is indicated by lamps 113, 114 and 115. The lamps 113, 114 and 115 are lit cumulatively corresponding to the then present speed of the fans in the machine.

It is desirable for the air flow of the present invention to be operating at its highest level when there is a large amount of human traffic through the room. To that end, a motion sensor 110 is positioned amid the indicator lights 17 on lower housing 13. The motion sensor may have an adjustment (not shown) to modify its operation depending upon the size of the room. In a room such as a hospital room, the sensor is aimed to perceive motion in high traffic areas such as the entryway rather than movement of the patient. In this position, it is most likely to detect entry of nurses, hospital support personnel, visitors and doctors, rather than motion of the patient in the bed. When sensor 110 detects the entry of such hospital personnel, or visitors, it sets the fan at its highest operating level, i.e., 700 ft.³/min. This assures the maximum germicidal activity when there is the greatest human activity in the room. At normal levels of traffic, such as during normal daytime hospital activity with only occasional visits by hospital personnel, the fans operate at a medium level of 500 ft.³/min. At night, where there is little or no activity, and thus no motion detected by sensor 110, the fan processes air at a low operating speed of 200 ft.³/min. The unit, through the microprocessor, surveys the room in 20 second intervals, and may adjust and/or temporarily shut down upon sequential information determined in the series of surveys.

It is known that as air temperature decreases a much higher level of ultraviolet exposure is necessary in order to have the desired kill rate. The internal air temperature sensor (not shown) may be mourned on deck assembly 30. As temperature decreases, it will automatically decrease fan speed preventing the high throughput rate until the room temperature rises as this is useful in conditions found in an air conditioned, fresh operating room or other hospital or office room after a period of non-use in air conditioned control.

Thus, once the on/off switch (not shown) is activated, the machine automatically adjusts the air speeds to take into account factors such as room occupancy and traffic and room temperature in order to assure the proper kill rate.

To protect against UV lamp failure, sensors 135 are positioned at the base of each UV lamp 60–65. When a bulb fails, lamp failure light 116 will flash. Failure is considered to be when a UV lamp falls more than 20% below normal. The pattern of flashing will vary depending on which of the UV lamps has failed. The lamp failure light will flash in groups of flashes, with the number of flashes in a group corresponding to the lamp position which is in failure. Thus, if the third lamp has failed, failure light 116 will flash in groups of three. Equally, sensors will indicate whether either one of the fans is not rotating at the intended level by flashing indicator 117.

There is an override of the system which will allow high speed operation regardless of room conditions. When button 118 is depressed, the machine will continue to operate at the highest level and will be so indicated by indicator lamp 119. Upon the next depression of push button 118 the machine will revert to automatic operation.

While the invention has been described as having a preferred design, it is understood that it is capable of further modification, uses and/or adaptations of the invention following in general the principal of the invention and including such departures from the present disclosure as come within known or customary practice in the art to which the invention pertains, as may be applied to the central figures hereinabove set forth and fall within the scope of the invention of the limits of the appended claims.

I claim:

1. An apparatus for germicidal cleansing of air comprising:

a housing;

a chamber in the housing;
   said housing and chamber each having first openings to allow air to enter the chamber and second openings to allow air to return to the environment surrounding the housing;

an ultraviolet light source positioned in the chamber;

the internal wall of the chamber is made from an ultraviolet reflective material; and the wall of the chamber is shaped to direct ultraviolet light incident upon the wall of the chamber uniformly throughout the chamber such that the energy in the chamber accumulates over time to reach a steady state energy level greater than that emitted by the UV source.

2. An apparatus according to claim 1 wherein the chamber is formed from spun aluminum.

3. An apparatus according to claim 1 wherein a fan is positioned at the second opening of said chamber to draw air from the exterior, through and out of the chamber.

4. An apparatus according to claim 3 wherein there are means to sense the human traffic near the apparatus and means to increase the speed of the fans as human traffic increases around the apparatus and to decrease the speed of the fans as human traffic decreases around the apparatus.

5. An apparatus according to claim 3 wherein there are means to decrease the speed of the fans as temperature of the air passing through the chamber decreases.

6. An apparatus according to claim 1 wherein a filter is positioned between the first opening in the housing and the first opening in the chamber to filter the air which is allowed to enter the chamber.

7. An apparatus according to claim 1 wherein the chamber is in the form of an ellipsoid with the first and second openings at either end of the ellipsoid along its major axis.

8. An apparatus according to claim 7 wherein external of the chamber, in proximity to and sufficiently spaced from the first and second openings in the chamber to permit air to enter and leave the chamber, are convex end caps which reflect any ultraviolet radiation in the chamber which escapes through said first and second opening, back into the chamber.

9. An apparatus according to claim 6 wherein the end caps are paraboloids having the same foci as the chamber.

* * * * *